US012778677B2

(12) United States Patent
Dufour et al.

(10) Patent No.: US 12,778,677 B2
(45) Date of Patent: Nov. 3, 2026

(54) METHOD AND SYSTEM FOR NAVIGATING A BONE MODEL IN COMPUTER-ASSISTED SURGERY

(71) Applicant: ORTHOSOFT ULC, Montreal (CA)

(72) Inventors: Marc-Antoine Dufour, Montreal (CA); Myriam Valin, Laval (CA); Jean-Sebastien Merette, Mont-St-Hilaire (CA); Pierre Couture, Montreal (CA); Martin Brummund, Montreal (CA)

(73) Assignee: ORTHOSOFT ULC, Montreal (CA)

( * ) Notice: Subject to any disclaimer, the term of this patent is extended or adjusted under 35 U.S.C. 154(b) by 1366 days.

(21) Appl. No.: 16/561,551

(22) Filed: Sep. 5, 2019

(65) Prior Publication Data

US 2020/0069372 A1 Mar. 5, 2020

Related U.S. Application Data

(60) Provisional application No. 62/727,287, filed on Sep. 5, 2018.

(51) Int. Cl.
*A61B 34/10* (2016.01)
*A61B 34/20* (2016.01)
(Continued)

(52) U.S. Cl.
CPC .............. *A61B 34/10* (2016.02); *A61B 34/20* (2016.02); *G06T 7/344* (2017.01); *G06T 17/00* (2013.01);
(Continued)

(58) Field of Classification Search
CPC ... A61B 34/10; A61B 34/20; A61B 2034/105; A61B 2034/108; A61B 2090/376;
(Continued)

(56) References Cited

U.S. PATENT DOCUMENTS 8,165,659 B2 4/2012 Sheffer et al.
2007/0270680 A1* 11/2007 Sheffer .................. A61B 90/36
600/407

(Continued)

OTHER PUBLICATIONS

Perrin et al. 2005 Computer Aided Surgery 10: 301-309 (Year: 2005).*

(Continued)

*Primary Examiner* — Keith M Raymond
(74) *Attorney, Agent, or Firm* — NORTON ROSE FULBRIGHT CANADA LLP

(57) ABSTRACT

A system for outputting a three-dimensional (3D) bone model of a patient during computer-assisted surgery comprises a processing unit and a non-transitory computer-readable memory communicatively coupled to the processing unit. Computer-readable program instructions executable by the processing unit are for: obtaining a 3D bone model of at least part of a bone of a patient, registering landmark points of the bone of the patient corresponding to the 3D bone model in a coordinate system tracking the bone, the landmark points being in an area of expected high accuracy in the 3D bone model, fitting the 3D bone model on the bone in the coordinate system tracking the bone, using the landmark points in the area of expected high accuracy, registering additional landmark points of the bone of the patient in the coordinate system tracking the bone, the additional landmark points being in an area of evolutive accuracy, assessing the accuracy of the additional landmark points by comparing the registration of the additional landmark points to the 3D bone model, updating at least part of the area of evolutive accuracy in the 3D bone model, and outputting the 3D bone model in the coordinate system tracking the bone with the updated area of evolutive accuracy, for subsequent navigation of the bone in computer-assisted surgery.

21 Claims, 4 Drawing Sheets

(51) Int. Cl.
*G06T 7/33* (2017.01)
*G06T 17/00* (2006.01)

(52) U.S. Cl.
CPC ... *A61B 2034/105* (2016.02); *A61B 2034/108* (2016.02); *G06T 2207/10116* (2013.01); *G06T 2207/30008* (2013.01); *G06T 2210/41* (2013.01)

(58) Field of Classification Search
CPC . A61B 34/25; A61B 34/30; A61B 2034/2048; A61B 2034/2055; G06T 7/344; G06T 17/00; G06T 2207/10116; G06T 2207/30008; G06T 2210/41; G06T 19/20; G06T 2219/2021
See application file for complete search history.

(56) References Cited

U.S. PATENT DOCUMENTS

2011/0085716 A1* 4/2011 Chefd'hotel .............. G06T 7/33 382/128
2011/0282473 A1* 11/2011 Pavlovskaia .............. G06T 7/12 700/98
2013/0096373 A1* 4/2013 Chabanas ................. G06T 7/75 600/101
2013/0329980 A1* 12/2013 Pekar ........................ G06T 7/33 382/131
2016/0089153 A1* 3/2016 Couture ............... A61B 17/157 606/88
2017/0132388 A1* 5/2017 Grady .................... G16H 50/50
2017/0323443 A1* 11/2017 Dhruwdas ............. G06T 7/0012
2018/0071032 A1* 3/2018 de Almeida Barreto .................... G06T 19/006
2018/0185100 A1* 7/2018 Weinstein .............. A61B 34/20

OTHER PUBLICATIONS

Zheng et al. 2014 Medical Physics 41:paper 081911 11pages (Year: 2014).*

* cited by examiner

METHOD AND SYSTEM FOR NAVIGATING A BONE MODEL IN COMPUTER-ASSISTED SURGERY

CROSS-REFERENCE TO RELATED APPLICATION

The present application claims the priority of U.S. Provisional Patent Application No. 62/727,287, filed on Sep. 5, 2018 and incorporated herein by reference.

TECHNICAL FIELD

The present application relates to image-based navigation and bone modelling in orthopedic computer-assisted surgery.

BACKGROUND OF THE ART

Imaging technologies are commonly used in the field of orthopedic surgery, for example in the planning leading to surgery. Various imaging modalities have historically been used, each with its own particularities. For example, Magnetic Resonance Imaging (MRI) may provide high-resolution imaging with high contrast between soft tissues and bone. MRI scans may have to date been preferred for bone model generation in medical imaging, due to the fact that the MRI scan images are capable of depicting cartilage as well as the bone. As an example, MRI scans can ensure the accuracy of the resulting surgery performed using patient-specific devices thus produced as having "negative" surfaces matching patient bone and cartilage. However, such MRI scans are both costly and time consuming to conduct. MRI may also involve more expensive equipment and may thus be less available. In contrast, radiographic equipment in its various forms or monikers (e.g., fluoroscope, Computed Tomography (CT), X-ray, C-arm) is more readily available but may provide a lesser resolution than MRI, notably in representing soft tissue. Due to availability of radiographic equipment, it may be desirable to devise methods for allowing computer-assisted navigation using radiographic equipment.

SUMMARY

In accordance with one aspect of the present disclosure, there is provided a system for outputting a three-dimensional (3D) bone model of a patient during computer-assisted surgery, comprising: a processing unit; and a non-transitory computer-readable memory communicatively coupled to the processing unit and comprising computer-readable program instructions executable by the processing unit for: obtaining a 3D bone model of at least part of a bone of a patient, registering landmark points of the bone of the patient corresponding to the 3D bone model in a coordinate system tracking the bone, the landmark points being in an area of expected high accuracy in the 3D bone model, fitting the 3D bone model on the bone in the coordinate system tracking the bone, using the landmark points in the area of expected high accuracy, registering additional landmark points of the bone of the patient in the coordinate system tracking the bone, the additional landmark points being in an area of evolutive accuracy, assessing the accuracy of the additional landmark points by comparing the registration of the additional landmark points to the 3D bone model, updating at least part of the area of evolutive accuracy in the 3D bone model, and outputting the 3D bone model in the coordinate system tracking the bone with the updated area of evolutive accuracy, for subsequent navigation of the bone in computer-assisted surgery.

In accordance with another aspect of the present disclosure, there is provided a system for outputting a three-dimensional (3D) bone model of a patient during computer-assisted surgery, comprising: a graphic-user interface; a processing unit; and a non-transitory computer-readable memory communicatively coupled to the processing unit and comprising computer-readable program instructions executable by the processing unit for: displaying a 3D bone model of at least part of a bone of a patient, displaying targets on the displayed 3D bone model, and registering landmark points of the bone of the patient corresponding to targets on the 3D bone model in a coordinate system tracking the bone, wherein targets in an area of expected high accuracy in the 3D bone model are at a lower density than targets in an area of evolutive accuracy; fitting the 3D bone model on the bone in the coordinate system tracking the bone, using the landmark points in the area of expected high accuracy, assessing the accuracy of the landmark points in the area of evolutive accuracy by comparing the registration of the landmark points to the 3D bone model, updating at least part of the area of evolutive accuracy in the 3D bone model, and outputting the 3D bone model in the coordinate system tracking the bone with the updated area of evolutive accuracy, for subsequent navigation of the bone in computer-assisted surgery.

In accordance with yet another aspect of the present disclosure, there is provided a system for outputting a three-dimensional (3D) bone model of a patient during computer-assisted surgery, comprising: a processing unit; and a non-transitory computer-readable memory communicatively coupled to the processing unit and comprising computer-readable program instructions executable by the processing unit for: obtaining a 3D bone model of at least part of a bone of a patient, registering landmark points of the bone of the patient corresponding to the 3D bone model in a coordinate system tracking the bone, the landmark points being in an area of expected high accuracy in the 3D bone model, fitting the 3D bone model on the bone in the coordinate system tracking the bone, using the landmark points in the area of expected high accuracy, registering additional landmark points of the bone of the patient in the coordinate system tracking the bone, the additional landmark points being in an area of evolutive accuracy, assessing the accuracy of the additional landmark points by comparing the registration of the additional landmark points to the 3D bone model, updating at least part of the area of evolutive accuracy in the 3D bone model, and outputting the 3D bone model in the coordinate system tracking the bone with the updated area of evolutive accuracy, for subsequent navigation of the bone in computer-assisted surgery.

DETAILED DESCRIPTION

Figure 1:
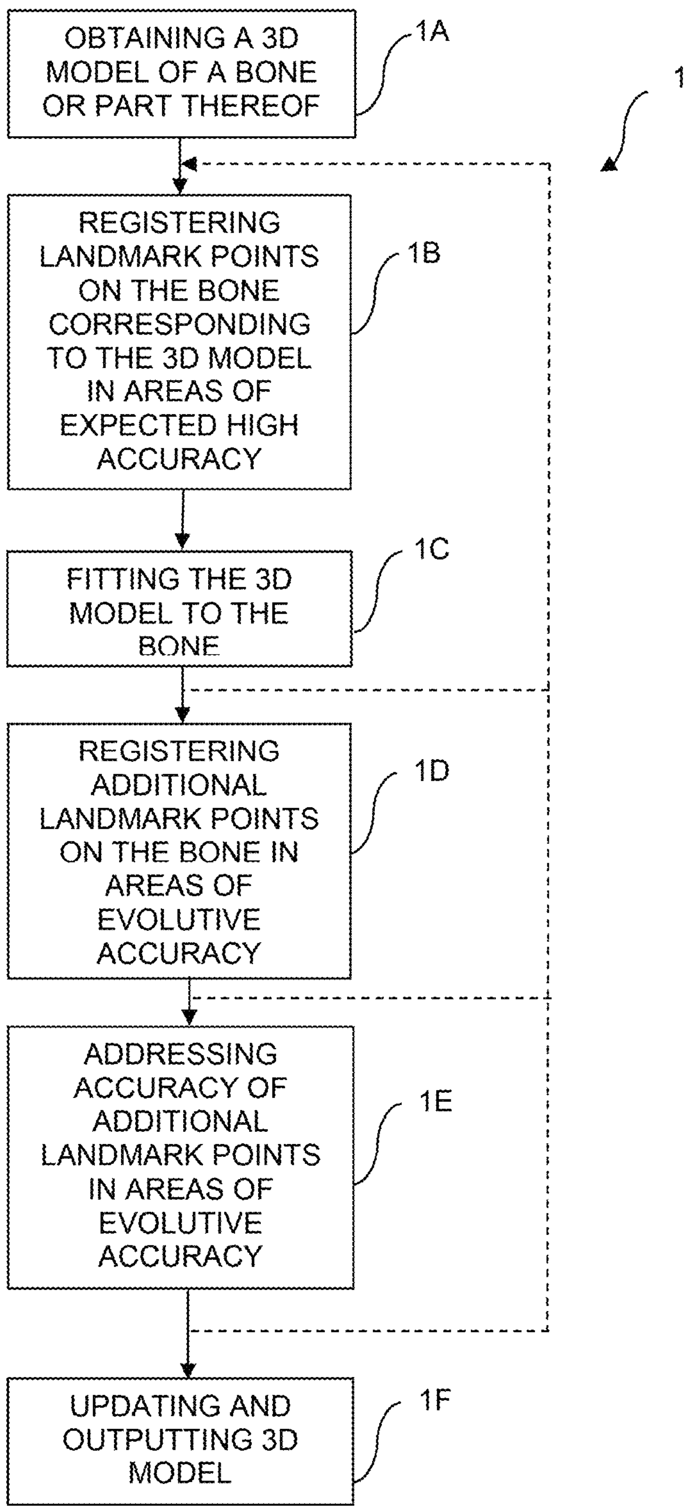
FIG. 1 is a flowchart depicting a method for updating and outputting a three-dimensional (3D) model of the bone for navigation during a surgical procedure, in accordance with the present disclosure.

Referring to the drawings and more particularly to FIG. 1, there is illustrated at 1 a method for updating and outputting a three-dimensional (3D) model of the bone during a surgical procedure. The method 1 may be performed at least partially by a computer-assisted surgery (CAS) system. An exemplary CAS system is generally shown at 10 in FIG. 2, and is used to perform orthopedic surgery maneuvers on a patient, including pre-operative registration and implant assessment planning, as described hereinafter. The CAS system 10 may consequently have one or more processing units dedicated to operating the method 1 and workflow of a surgical procedure. The CAS system 10 may therefore include a non-transitory computer-readable memory communicatively coupled to the one or more processing units and may comprise computer-readable program instructions executable by the one or more processing units to operate the method 1 described herein. In an embodiment, the CAS system 10 drives a surgical robot used autonomously, and/or as an assistive or collaborative tool for an operator (e.g., surgeon). In another embodiment, the CAS system 10 is one used without robotic assistance, and assists operator by way of surgical navigation.

According to 1A, a 3D model of a bone or part thereof is obtained. Reference is made herein to a 3D model of the bone for simplicity. However, the 3D model may be for a part of a bone only, such as the region of interest that will be altered during surgery (e.g., resected, cut, rasped, resurfaced), for example to receive an implant. Therefore, the expression "3D model of a bone" may include parts of a bone, and may also include other tissues on the bone, such as cartilage, osteophytes, etc.

Obtaining the 3D model of the bone or part thereof as in 1A may entail performing the imaging with imaging equipment, and generating the 3D bone model from the imaging. The imaging equipment may be part of the CAS system 10 (FIG. 2) or may be dedicated imaging equipment, for instance in a pre-operative imaging session, in the form of a surgical planning computer program and/or an imaging system. The imaging modalities used to image and generate the 3D model may include MRI, radiographic equipment, etc.

In accordance with an embodiment, the 3D model of the bone results from two or more X-rays only. At least two or more X-ray images are required of the patient's bone or bones, which must be taken from different angular positions (e.g. one lateral X-ray and one frontal or anterior X-ray) or points of view (POV). While one X-ray image may be insufficient, more than two X-ray images may alternately be used. Generally, the greater the number of X-ray scans taken from different angular positions or points of view (POV) e.g. lateral, medial, anterior, posterior, etc., the greater the resulting accuracy of the digital bone model created therefrom. However, the desired accuracy has been found to be obtainable when only two X-rays are taken from transversely (e.g., perpendicularly) disposed angular positions (e.g. lateral or medial POV and frontal/anterior or posterior POV). Moreover, the method 1 may compensate for inaccuracies with its evolutive registration steps performed subsequently to update the 3D bone model. Using the two-dimensional (2D) X-ray images, the 3D model may be generated and may take the form of a digital bone model, also generated as part of 1A. Therefore, the generation of the digital 3D bone model may be based solely on the X-ray scan, with two points of view sufficient in some instance. The generation of the digital 3D bone model may also include merging the patient bone images to generic models that generally match the patient's anatomical features, or to models obtained from a bone atlas or like database of bone models. The obtaining of the 3D bone model as in 1A, including the imaging and the generation of the 3D bone model may be as described in U.S. Pat. No. 9,924,950, incorporated herein by reference. Some of the actions in 1A may be done preoperatively, such as the imaging and the generation of the 3D bone model. Obtaining the 3D model of the bone may be done intraoperatively by the CAS system 10.

Thus, although other imaging modalities may be used, such as MRI, the presently described method and CAS system 10 enables the creation and use of a 3D bone model generated using only two-dimensional (2D) X-ray images of the specific patient's bone(s). This may enable a smaller delay between preoperative planning and surgical procedure, and in a more cost effective manner than with known prior art systems and methods, which involve the use of MRI scans to produce the digital bone models.

Figure 2:
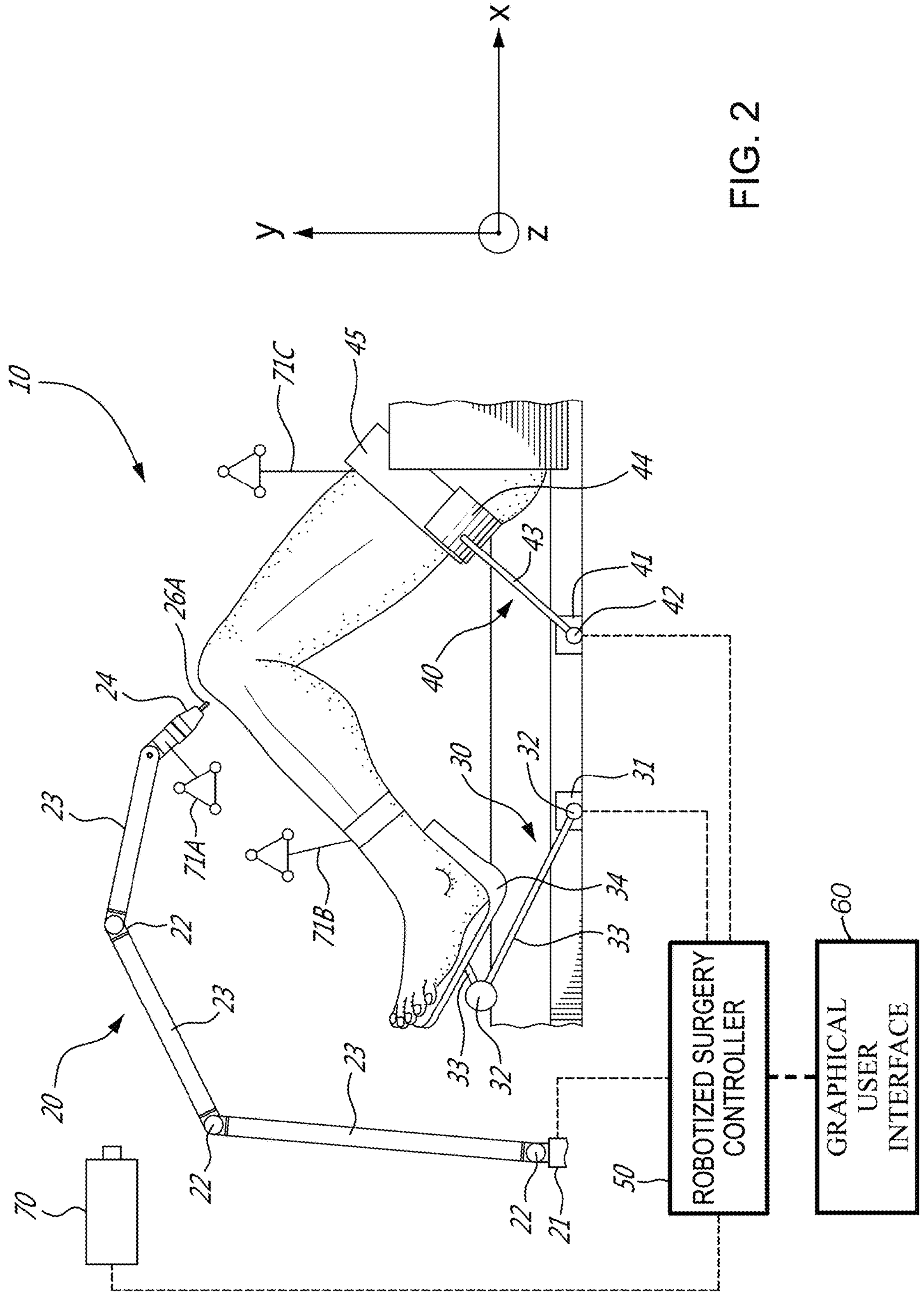
FIG. 2 is a schematic view of a CAS system in accordance with the present disclosure.
Figure 3:
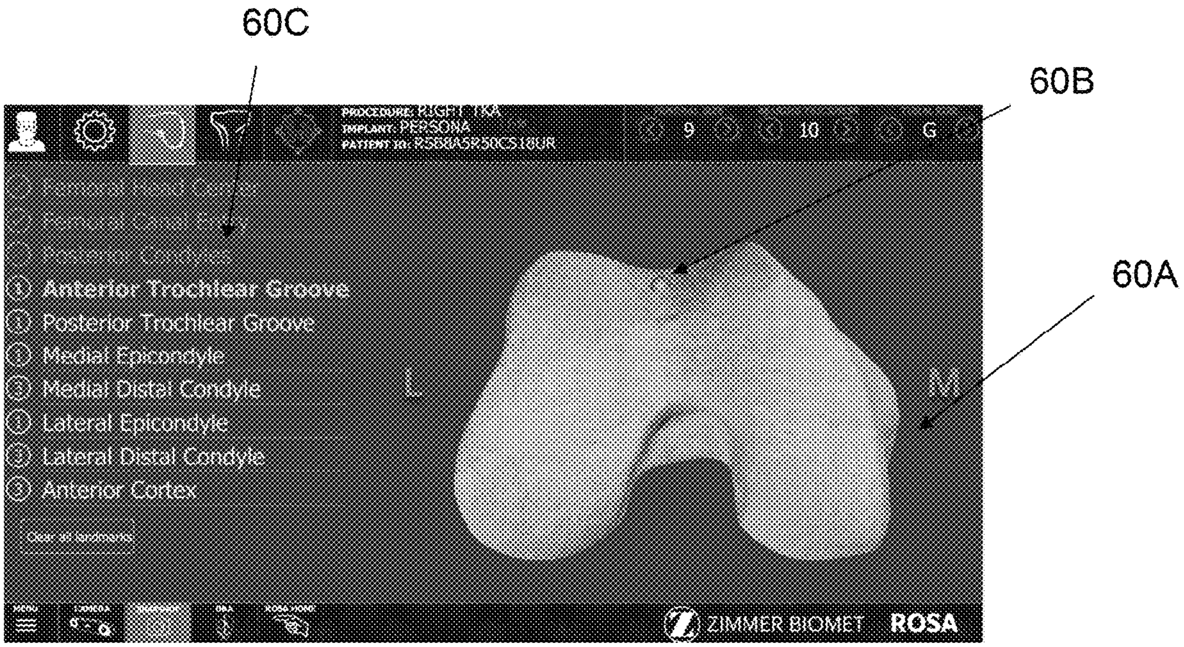
FIG. 3 is an exemplary screen shot of a graphic-user interface of the CAS system during the method of FIG. 1, showing a femur from a caudal point of view.
Figure 4:
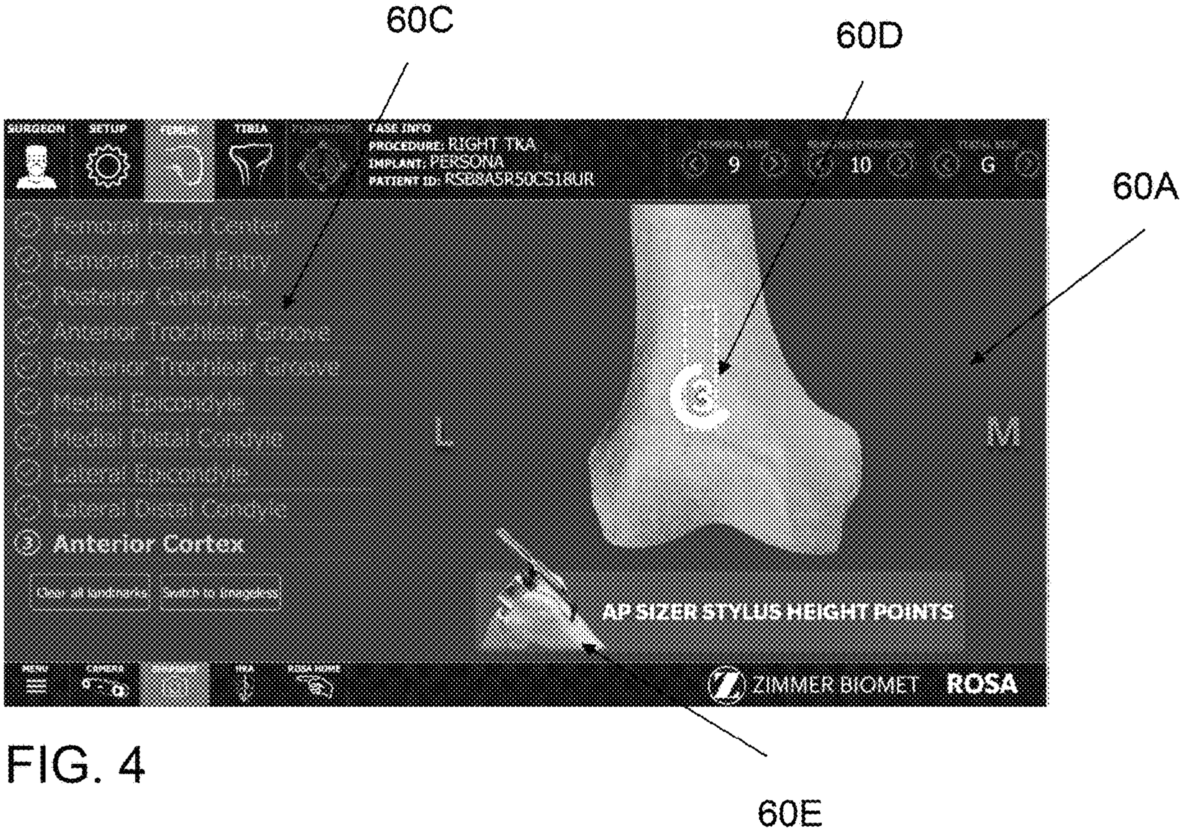
FIG. 4 is an exemplary screen shot of the graphic-user interface of the CAS system during the method of FIG. 1, showing a femur from an anterior point of view.
Figure 5:
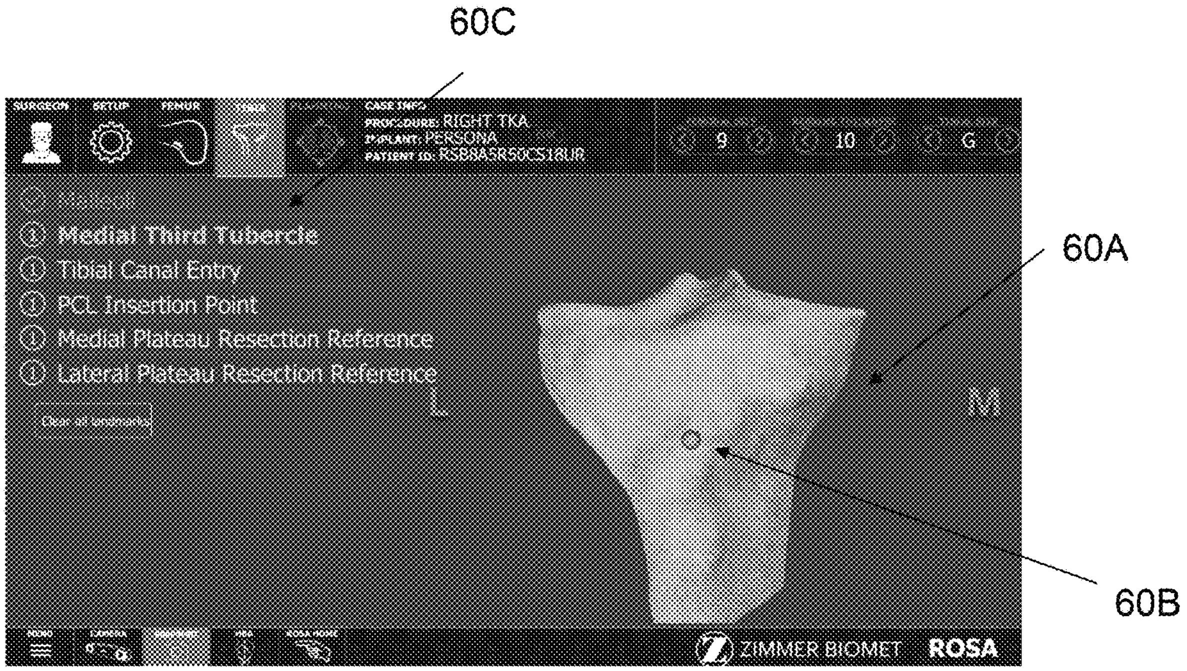
FIG. 5 is an exemplary screen shot of a graphic-user interface of the CAS system during the method of FIG. 1, showing a tibia from an anterior point of view.

According to 1B, landmark points are registered on the actual bone in an area corresponding to the bone part imaged by the 3D model. This may be done intraoperatively, with the bone exposed through commencement of the surgical procedure. Registration may also be known as digitizing, and may be defined as recording coordinates of a point or surface in a referential coordinate system, also known as a frame of reference. In FIG. 2, a x,y,z coordinate system is shown, and is a virtual coordinate system, and registration may be recording x,y,z points in the x,y,z coordinate system, as an example. Depending on the type of procedure, the registration may entail a robotic or manual manipulation of a registration pointer contacting points on the surface of the bone, including cartilage, for the points to be registered (i.e., recorded, digitized). Registration may also be done by ranging, for example using a laser with ranging capability (e.g., measuring a distance). Stated differently, registration described herein may be contactless, namely in the form of a radiation transmitter, for example a light transmitter, such as a laser beam, coupled to a distance sensor. In particular, said identification means can be in the form of a laser telemeter. In an embodiment, the laser is manipulated by a robotic arm. Therefore, the method 10 may include a displaying of the 3D model on a graphic-user interface (GUI), such as shown in FIGS. 3-5 and detailed hereinbelow. The displaying may begin when or after the 3D model is obtained in 1A. The displaying may be continuous during registration steps, at least, though some pauses may occur, for instance when switching the registration from a bone to another. The displaying may be performed by the CAS system for a manual registration and optionally for a robotic registration. In the case of a robotic registration, the displaying may allow an operator to visualize the accuracy of the robot. Still further in the case of a robotic registration, the displaying may assist an operator in manipulating the robotic arm in an assistive or collaborative mode. The registration of the points in 1B may require that the bone is tracked as part of a localized or global coordinate system, a.k.a., a reference frame or frame of reference). Examples of the tracking technologies are described with the CAS system 10 in FIG. 2, and may include optical tracking, inertial sensors, 3D cameras, infrared ranging, robotized components. The points may for instance take the form of x,y,z coordinates relative to the bone or to a fixed referential featuring the bone. A set of numerous points may consequently be a point cloud.

According to an embodiment, the landmark points registered are at areas of expected high accuracy in the digital bone model. For example, if the 3D model was generating solely from X-ray images, some parts of the bone model featuring cartilage or other soft tissue may not be as accurate as parts of the bone in which cortical bone is exposed free of cartilage. Such areas exposing bone matter as opposed to cartilage may be referred to as areas of expected high accuracy on the digital bone model generated by the X-ray scans. These areas of expected high accuracy on the digital bone model may generally correspond to points on a peripheral bone contour in at least one of the angular positions from which an X-ray image is taken. For example, if a frontal, or anterior, X-ray has been taken of the bone, the medial, lateral and proximal outer peripheral contours of the bone will be expected to have high accurate in the X-ray image and thus in the resulting digital bone model created thereby. As a result, points on the bone model which are disposed along these medial, lateral and/or proximal peripheral contours of the digital bone model will be areas of expected high accuracy, even if the X-ray image is not capable of revealing any cartilage present. Similarly, if a lateral X-ray has been taken of the bone, the anterior, distal and/or proximal outer peripheral contours of the bone will be very accurate in the X-ray image, and thus in the resulting digital bone model created thereby. As a result, points on the bone model which are substantially disposed along these anterior, distal and proximal outer peripheral contours of the digital bone model will be areas of expected high accuracy, even if the X-ray image is not capable of revealing any cartilage present. Thus, by registering the landmark points on the bone surface in 1B, which landmark points fall in these areas of expected high accuracy on the bone model, the landmark points on the actual bone are deemed to be accurately depicted by the 3D model without any appreciable loss in accuracy. While the description provided above pertains to X-ray imaging, the same may apply to MRI, in which cortical bone landmarks may be preferred over softer cartilage surfaces. Therefore, the same concept of preferred landmark points may be applied to 1B in the case of a 3D model generated from MRI.

As an example, the method 1 and the CAS system 10 may provide visual guidance, for instance by way of a visual representation of the bone model to indicate areas of the bone in which landmark points should be registered, as in FIGS. 3-5 on a GUI. Such an arrangement may be applicable to a manual navigation in surgery, or to robotics as well. In an embodiment, targets are successively identified on the bone model of the GUI, for landmarks to be registered. In an embodiment, the CAS system displays consecutive landmarks in the areas of expected high accuracy that are separated by a high-accuracy distance, for instance of at least 15 mm. In an embodiment, the high-accuracy distance is of 20±4 mm.

According to 1C, the 3D model may be fitted to the bone using the registered landmark points of 1B. The fitting of the 3D model to the bone requires obtaining a sufficient number of points such that the CAS system 10 may match a surface of the 3D model and a corresponding surface generated from the registered landmark points. For example, the CAS system 10 may form a cloud of points that will be sufficiently accurate for overlaying the 3D model over the bone.

The step 10 of fitting the 3D bone model to the bone may include positioning and orienting the 3D bone model such that it becomes part of the coordinate system of the bone, i.e., points on the 3D bone model are given an x,y,z coordinate. To reduce error or to lessen the number of landmark points required in 1B, 10 may include the guidance data, used in providing the visual guidance on the GUI or robotic instructions, to lessen the range of the fitting function. For instance, if the guidance data guides an operator in registering landmark points on a particular prominent bone feature (e.g., an epicondyle), the fitting may use an identification of such bone feature in the 3D bone model, thereby reducing substantially the range of fitting possibilities, and accelerating the fitting process. At the outset of 1C, the 3D model is fitted on the bone in the intra-operative coordinate system tracked by the CAS system 10.

According to 1D, in spite of having the 3D bone model fitted to the bone and tracked in the intra-operative coordinate system relative the bone, additional landmark points on the bone are registered. This may include points of evolutive accuracy in contrast to the areas of expected high accuracy of 1B. For example, areas of evolutive accuracy may be defined as surfaces of the bone featuring cartilage and other soft tissues. The areas of evolutive accuracy may also be surfaces that are not directly visible through the POVs of the radiographic equipment, or that are not prominent, such as notches and grooves, for example the anterior femoral cortex, trochlear (patellar) groove, intercondylar fossa, etc. Stated differently, evolutive accuracy refers to areas in which it is possible that position points need to be corrected, or "evolve" toward greater accuracy. The evolutive accuracy may also be put in perspective with the areas of expected high accuracy of 1B, in which there will or should not be any evolution of the point positions on the surfaces. According to an embodiment, 1D is dedicated to registering landmark points in the areas of evolutive accuracy, as the method 1 and the CAS system 10 may rely on the areas of expected high accuracy of the 3D bone model as being representative of the actual bone and thus skip at the outset of 1D registration of points in the area of high accuracy. This may reduce the number of points registered as the registration of redundant points may be reduced, unnecessary or avoided. The method 1 and the CAS system 10 may provide visual guidance through the GUI during 1D, for instance by way of a visual representation of the bone model to indicate the target locations of the bone in which landmark points should be registered. Such an arrangement may be applicable to a manual navigation in surgery or robotics also. In an embodiment, targets are successively identified on the areas of evolutive accuracy of the bone model, for landmarks to be registered. In an embodiment, CAS system displays consecutive landmarks in the areas of evolutive accuracy that are separated by an evolutive-accuracy distance, for instance of less than 15 mm. In an embodiment, the evolutive-accuracy distance is of 5±3 mm. Generally speaking, the high-accuracy distance between landmarks of the high-accuracy area is greater than the evolutive-accuracy distance between landmarks of the evolutive-accuracy area. Stated differently, a lesser density of landmarks is registered in 1B than in 1D. Moreover, a total number of registered landmarks is less than a similar procedure without the dual concept of high-accuracy area and evolutive-accuracy area.

By way of example, in the case of a femur, the areas of expected high accuracy may include the anterior and posterior femur surfaces, the condyles, the epicondyles in medio-lateral view. In a knee application, the tibial plateaus may be described as zones of evolutive accuracy due to the presence of the meniscus. Exemplary registration procedures are described below relative to the GUI of FIGS. 3-5.

As per 1E, as the additional landmark points on the bone are registered, the accuracy of the additional landmark points is assessed by the CAS system 10. For instance, the 3D bone model may have tolerances for the points of its area(s) of evolutive accuracy. This may be in the form of a matrix with upper and lower bounds for the bone model that may be used in 1E to identify certain landmark points that should be retaken during registration. 1E may determine if the position of the additional landmark points are within the accepted tolerances to accept the registration, and update the coordinates of points or keep the coordinates provided by the 3D bone model. As an example, 1D and 1E may be done in alternating repeated sequence, on a point by point basis. 1E may also be done after a sufficient representation of an area of evolutive accuracy has been registered in 1D. By analyzing a subarea of evolutive accuracy, the method 1 and CAS system 10 may observe a localized surface deviation with respect to the equivalent area on the bone model, and this may result in an update of the bone model, in 1F.

According to an embodiment, in the case of a distal femur, the areas of expected high accuracy that are used in 1B are the medial and lateral epicondyles, and end surfaces of the lateral and medial condyles. The areas of evolutive registration may be any of anterior femoral cortex, trochlear (patellar) groove, intercondylar fossa, for example. These surfaces may evolve intraoperatively after the fitting of 1C, when points taken intraoperatively do not match the points of the 3D model as fitted to the bone.

Still according to 1E, if a given threshold number of landmark points in the evolutive registration are within tolerances, the assessment of 1E may be completed. Such threshold number of landmark points may require a sufficient distribution of landmark points over the area of evolutive registration.

1E may entail guiding the operator, by visual display on the GUI for example, in registering once more a point to verify the accuracy, for instance if the coordinates of the landmark point fall outside of the tolerances. This may be done for the areas of evolutive accuracy, but also for some points or areas of expected high accuracy. According to an embodiment, the tolerances may be substantially smaller for the areas of expected high accuracy as it is anticipated that the areas of expected high accuracy are accurate. The assessment of 1E may also lead to a request for registering additional points in the close proximity of the first one. In the instance in which the registration is done by robot, 1E may cause movement instructions to be sent to a controller of the robotic arm to digitize points in close proximity. In an embodiment in which a human manipulator of a registration tool is involved, 1E may provide visual guidance to the operator to identify the target areas that should be digitized, and this includes the areas of evolutive accuracy, but also the areas of expected high accuracy, for instance on the GUI. Compared to standard navigation, live feedback may be provided to the operator on the quality of the landmark—e.g., "this landmark was not good, retake recommended," or in similar driving instructions for a robotic platform. In an embodiment, target points on the GUI may use a colour scheme to guide the operator: e.g., "red" target, retake; "yellow" target, being verified under 1E; "green target", proceed or accepted. This is an example among others. The operator or robotic platform may be prompted to just retake a few points as the landmark points are being taken, in contrast to having to redo the entire registration at the end. This may result in a lesser number of landmark points having to be registered.

According to 1F, the 3D model is updated and outputted, as a result of the actions and instructions of 1E. 1D, 1E and/or 1F may be done in alternating repeated sequence, on a point by point basis. Moreover, the registrations of 1B and 1D may be done simultaneously or in any appropriate sequence (e.g., three points of 1B, two points of 1D, two points of 1B, etc), with the fitting of 1C occurring when a number of landmark points allowing sufficient fitting accuracy is attained. 1E may also occur at any point during the registration of points of 1B and 1D, if the point taking is mixed. 1F may also be done after a sufficient representation of an area of evolutive accuracy has been assessed in 1E. In an example, the 3D model may be updated in an evolutive manner as the landmark points are taken. Likewise, the outputting of the 3D model may include real-time adjustment based on the assessment of 1E. The outputting 3D may include displaying an updated version of the 3D model, or navigation values taking into consideration the updates.

At the outset of 1F, the 3D model may be outputted in different forms. For example, the output may be in the form of a visual representation or a cloud point set of the updated 3D model in the coordinate system during surgery to guide an operator in navigation of the bone. The 3D model may be outputted for subsequent uses or to create patient-specific tools. The updated 3D model may also be used to determine the location of cut planes, for instance with the use of digital models of implants. The cut planes may be in the form of instructions for a robotic arm, or as navigation data for an operator.

Consequently, the method 1 may increase the accuracy of the digital 3D bone model. The evolutive registration of the method 1 relies on higher quality landmarks, i.e. in the areas of expected high accuracy, to perform a fitting and rely on the bone model to accept the accuracy of entire surfaces of the bone, such as well-defined protrusions visible from the two 2D Xray POVs. The method 1 may then aim to build on the lower resolution areas, i.e., the areas of evolutive accuracy.

Referring to FIG. 2, the CAS system 10 may be used to perform at least some of the steps of method 1 of FIG. 1. The CAS system 10 is shown relative to a patient's knee joint in supine decubitus, but only as an example. The system 10 could be used for other body parts, including non-exhaustively hip joint, spine, and shoulder bones.

The CAS system 10 may be robotized, in which case it may have a robot arm 20, a foot support 30, a thigh support 40, a CAS controller 50, and a GUI 60:

- The robot arm 20 is the working end of the system 10, and is used to perform bone alterations as planned by an operator and/or the CAS controller 50 and as controlled by the CAS controller 50;
- The foot support 30 supports the foot and lower leg of the patient, in such a way that it is only selectively movable. The foot support 30 is robotized in that its movements can be controlled by the CAS controller 50;
- The thigh support 40 supports the thigh and upper leg of the patient, again in such a way that it is only selectively or optionally movable. The thigh support 40 may optionally be robotized in that its movements can be controlled by the CAS controller 50;
- The CAS controller 50 operates the surgical workflow and at least part of the method 1. The CAS controller 50 may also control the robot arm 20, the foot support 30, and/or the thigh support 40. The CAS controller 50 may also guide an operator through the surgical procedure, by providing intraoperative data of position and orientation, and may therefore have the appropriate interfaces such as mouse, footpedal etc;

A GUI 60 provides visual guidance through the workflow of the CAS system 10, and/or during the method 1. The GUI 60 may be part of a monitor, touchscreen, tablet, etc; and The tracking apparatus 70 may be used to track the bones of the patient, and the robot arm 20 if present. For example, the tracking apparatus 70 may assist in performing the calibration of the patient bone with respect to the robot arm, for subsequent navigation in the X, Y, Z coordinate system.

The CAS system 10 may be without the robot arm 20, with the operator performing manual tasks. In such a scenario, the CAS system 10 may only have the CAS controller 50, GUI 60 and the tracking apparatus 70. The CAS system 10 may also have non-actuated foot support 30 and thigh support 40 to secure the limb.

Still referring to FIG. 2, a schematic example of the robot arm 20 is provided. The robot arm 20 may stand from a base 21, for instance in a fixed relation relative to the operating-room (OR) table supporting the patient. The relative positioning of the robot arm 20 relative to the patient is a determinative factor in the precision of the surgical procedure, whereby the foot support 30 and thigh support 40 may assist in keeping the operated limb fixed in the illustrated X, Y, Z coordinate system, used by the method 1. The robot arm 20 has a plurality of joints 22 and links 23, of any appropriate form, to support a tool head 24 that interfaces with the patient. The tool head 24 may be a registration pointer, rod or wand, ranging laser, radiation/light transmitter, laser telemeter, to perform the palpating of the registration of 1B and 1E of method 1.

The arm 20 is shown being a serial mechanism, arranged for the tool head 24 to be displaceable in a desired number of degrees of freedom (DOF). For example, the robot arm 20 controls 6-DOF movements of the tool head 24, i.e., X, Y, Z in the coordinate system, and pitch, roll and yaw. Fewer or additional DOFs may be present. For simplicity, only a generic illustration of the joints 22 and links 23 is provided, but more joints of different types may be present to move the tool head 24 in the manner described above. The joints 22 are powered for the robot arm 20 to move as controlled by the controller 50 in the six DOFs. Therefore, the powering of the joints 22 is such that the tool head 24 of the robot arm 20 may execute precise movements, such as moving along a single direction in one translation DOF, or being restricted to moving along a plane, among possibilities. Such robot arms 20 are known, for instance as described in U.S. patent application Ser. No. 11/610,728, incorporated herein by reference.

In order to preserve the fixed relation between the leg and the coordinate system, and to perform controlled movements of the leg as described hereinafter, a generic embodiment is shown in FIG. 2. The foot support 30 may be displaceable relative to the OR table, in order to move the leg in flexion/extension (e.g., to a fully extended position and to a flexed knee position), with some controlled lateral movements being added to the flexion/extension. Accordingly, the foot support 30 is shown as having a robotized mechanism by which it is connected to the OR table, with sufficient DOFs to replicate the flexion/extension of the lower leg. Alternatively, the foot support 30 could be supported by a passive mechanism, with the robot arm 20 connecting to the foot support 30 to actuate its displacements in a controlled manner in the coordinate system. The mechanism of the foot support 30 may have a slider 31, moving along the OR table in the X-axis direction. Joints 32 and links 33 may also be part of the mechanism of the foot support 30, to support a foot interface 34 receiving the patient's foot. Moreover, while the leg is shown, the method 1 and CAS system 10 could be used to perform orthopedic surgery on other body parts (e.g. shoulder).

Referring to FIG. 2, the thigh support 40 may be robotized, static or adjustable passively. In the latter case, the thigh support 40 may be displaceable relative to the OR table, in order to be better positioned as a function of the patient's location on the table. Accordingly, the thigh support 40 is shown as including a passive mechanism, with various lockable joints to lock the thigh support 40 in a desired position and orientation. The mechanism of the thigh support 40 may have a slider 41, moving along the OR table in the X-axis direction. Joints 42 and links 43 may also be part of the mechanism of the thigh support 40, to support a thigh bracket 44. A strap 45 can immobilize the thigh/femur in the thigh support 40. The thigh support 40 may not be necessary in some instances. However, in the embodiment in which the range of motion is analyzed, the fixation of the femur via the thigh support 40 may assist in isolating joint movements.

The CAS controller 50 has a processor unit to control movement of the robot arm 20, and of the leg support (foot support 30 and thigh support 40), if applicable. The CAS controller 50 provides computer-assisted surgery guidance to an operator, whether in the form of a navigation data, model assessment, etc in pre-operatively planning or during the surgical procedure. The system 10 may comprise various types of interfaces, for the information to be provided to the operator, for instance via the GUI 60. The interfaces of the GUI 60 may be monitors and/or screens including wireless portable devices (e.g., phones, tablets), audio guidance, LED displays, among many other possibilities. If a robot arm 20 is present, the controller 50 may then drive the robot arm 20 in performing the surgical procedure based on the planning achieved pre-operatively. The controller 50 may do an intra-operative bone model assessment to update the bone model and fit it with accuracy to the actual bone, and hence enable corrective plan cuts to be made, or guide the selection of implants. The controller 50 may also generate a post-operative bone model. The CAS controller 50 runs various modules, in the form of algorithms, code, non-transient executable instructions, etc, in order to operate the system 10 in the manner described herein.

The use of the tracking apparatus 70 may provide tracking data to perform the bone model updating and subsequent surgical navigation. For example, the tracking apparatus 70 may assist in performing the calibration of the patient bone with respect to the coordinate system, for subsequent navigation in the X, Y, Z coordinate system. According to an embodiment, the tracking apparatus 70 comprises a camera that optically sees and recognizes retro-reflective references 71A, 71B, and 71B, so as to track the tools and limbs in six DOFs, namely in position and orientation. In an embodiment featuring the robot arm 20, the reference 71A is on the tool head 24 of the robot arm 20 such that its tracking allows the controller 50 to calculate the position and/or orientation of the tool head 24 and tool 26A thereon. Likewise, references 71B and 71C are fixed to the patient bones, such as the tibia for reference 71B and the femur for reference 71C. In an embodiment without the robot arm 20, references such as reference 71A are on the navigated tools (including a registration tool) such that their tracking allows the controller 50 to calculate the position and/or orientation of the tools and register points. Likewise, references 71B and 71C may be fixed to the patient bones, such as the tibia for reference 71B and the femur for reference 71C. As shown, the references 71 attached to the patient need not be invasively anchored to the bone, as straps or like attachment means may provide sufficient grasping to prevent movement between the references 71 and the bones, in spite of being attached to soft tissue. However, the references 71B and 71C could also be secured directly to the bones. Therefore, the controller 50 continuously updates the position and/or orientation of the robot arm 20 and patient bones in the X, Y, Z coordinate system using the data from the tracking apparatus 70. As an alternative to optical tracking, the tracking system 70 may consist of inertial sensors (e.g., accelerometers, gyroscopes, etc) that produce tracking data to be used by the controller 50 to continuously update the position and/or orientation of the robot arm 20. Other types of tracking technology may also be used.

Some of the steps of method 1 may be achieved in the manner described above, with the robot arm 20 using a registration pointer on the robot arm 20, and with the assistance of the tracking apparatus 70 if present in the robotized surgery system 10. Another calibration approach is to perform radiography of the bones with the references 71 thereon, at the start of the surgical procedure. For example, a C-arm may be used for providing suitable radiographic images. The images are then used for the surface matching and fitting with the bone model of the patient.

Examples of steps of the method 1 and of the GUI 60 of FIG. 2 are shown in FIGS. 3-5, relative to a femur and to a tibia. With reference to FIGS. 3-5, the GUI 60 may have a main view 60A where the bone model is displayed. A target 60B may be shown on the bone model, whether it be for the registration of 1B, 1D or 1E. A menu 60C may also be present in the GUI 60. The menu 60C may indicate the regions of the bone (i.e., anatomical regions, in contrast to the areas of 1B and 1D) on which points must be registered. As the registration in a region is completed, a check logo may be provided, and/or other completion features may be used (e.g., green colour). The regions of the bone may in an example each be associated with a given view (e.g., zoom) and/or a given POV. If the operator selects a region, the POV of the model may change to show the target landmark points in the region.

Referring to FIG. 4, a zone 60D may also be shown on the bone model. Such a zone may be regarded as an area of evolutive accuracy, in which a higher density of points must be registered. A number may be displayed to indicate the number of points that remain to be registered. Warning signals may be addressed to an operator if the points are adjudged to be outside of the zone. A panel 60E on the GUI 60 may provide guidance as to a tool that needs to be used for the registration. As an example, an anterior-posterior sizer stylus may be recommended to register height points. As another example related to knee surgery, a registration tool with feet (i.e. claw tool) may be used to digitize the posterior condyles.

Examples of points that may be registered in the method 1 of FIG. 1 for the femur may be as follows, just as an example: the area of high accuracy may include the anterior and posterior trochlear groove, trochlear groove points in the deepest portion of the trochlear groove, medial and lateral epicondyles, medial and lateral distal condyles. The anterior and posterior trochlear groove points are used to determine the anterior-posterior axis, which is used for the femoral rotational alignment. The medial and lateral epicondyles points may be used to determine the epicondylar axis, which is used for the femoral rotational alignment. The M/L sizing of the femoral component may be suggested based on these registered landmark points. Referring to FIG. 5, the GUI 60 is shown displaying the tibia. In order to recreate the mechanical axis of the tibia, two points are digitized on the medial and lateral malleoli, as they may be regarded as high accuracy landmark points.

The invention claimed is:

1. A system for outputting a three-dimensional (3D) bone model of a patient during computer-assisted surgery, comprising:
- a processing unit; and
- a non-transitory computer-readable memory communicatively coupled to the processing unit and comprising computer-readable program instructions executable by the processing unit for:
- obtaining a 3D bone model of at least part of a bone of a patient, the 3D bone model being specific to the patient, the 3D bone model resulting from pre-operative imaging, the 3D bone model having at least an area of expected high accuracy and at least an area of evolutive accuracy, a difference in accuracy between areas being a result of visibility from the pre-operative imaging resulting in inaccuracies of bone representation in the area of evolutive accuracy,
- with the 3D bone model having the inaccuracies of bone representation in the area of evolutive accuracy, registering landmark points of the bone of the patient corresponding to the 3D bone model in a coordinate system tracking the bone, the landmark points being in the area of expected high accuracy in the 3D bone model,
- fitting the 3D bone model on the bone in the coordinate system tracking the bone, using the landmark points in the area of expected high accuracy,
- registering additional landmark points of the bone of the patient in the coordinate system tracking the bone, the additional landmark points being in the area of evolutive accuracy,
- assessing the accuracy of the additional landmark points by comparing the registration of the additional landmark points to the 3D bone model,
- updating at least part of the area of evolutive accuracy in the 3D bone model, and
- outputting the 3D bone model in the coordinate system tracking the bone with the updated area of evolutive accuracy, for subsequent navigation of the bone in computer-assisted surgery.

2. The system according to claim 1, wherein obtaining the 3D bone model includes generating the 3D bone model from X-ray images specific to the patient.

3. The system according to claim 2, wherein generating the 3D bone model from X-ray images includes generating the 3D bone model from only two X-ray images.

4. The system according to claim 1, wherein registering the landmark points in the area of expected high accuracy includes registering a high-accuracy density of points, and wherein registering the additional landmark points in the area of evolutive accuracy includes registering an evolutive-accuracy density of points.

5. The system according to claim 4, wherein registering includes registering the evolutive-accuracy density of points being greater than high-accuracy density of points.

6. The system according to claim 4, wherein registering the additional landmark points in the area of evolutive accuracy includes registering the additional landmark points at a distance of 5±3 mm.

7. The system according to claim 6, wherein registering the landmark points in the area of expected high accuracy includes registering the landmark points at a distance of 20±4 mm.

8. The system according to claim 1, wherein registering one of the additional landmark points in the area of evolutive accuracy occurs between registering two of the landmark points in the area of expected high accuracy.

9. The system according to claim 1, wherein assessing the accuracy of the additional landmark points includes verifying if the additional landmark points fall within tolerances of the area of the evolutive accuracy.

10. The system according to claim 9, wherein verifying if the additional landmark points fall within tolerances of the area of the evolutive accuracy includes rejecting at least one of the additional landmark points and registering at least another one of the additional landmark points in proximity to a rejected landmark point.

11. The system according to claim 1, further comprising displaying the 3D bone model with the updated area of evolutive accuracy.

12. The system according to claim 1, further comprising tracking a tool relative to the updated area of evolutive accuracy on the bone.

13. A system for outputting a three-dimensional (3D) bone model of a patient during computer-assisted surgery, comprising:

a graphic-user interface;

a processing unit; and a non-transitory computer-readable memory communicatively coupled to the processing unit and comprising computer-readable program instructions executable by the processing unit for:

displaying a 3D bone model of at least part of a bone of a patient, the 3D bone model being specific to the patient, the 3D bone model resulting from pre-operative imaging, the 3D bone model having at least an area of expected high accuracy and at least an area of evolutive accuracy, a difference in accuracy between areas being a result of visibility from the imaging;

displaying targets on the displayed 3D bone model having the difference in accuracy, and registering landmark points of the bone of the patient corresponding to targets on the 3D bone model in a coordinate system tracking the bone, wherein targets in the area of expected high accuracy in the 3D bone model are at a lower density than targets in the area of evolutive accuracy;

fitting the 3D bone model on the bone in the coordinate system tracking the bone, using the landmark points in the area of expected high accuracy, assessing the accuracy of the landmark points in the area of evolutive accuracy by comparing the registration of the landmark points to the 3D bone model, updating at least part of the area of evolutive accuracy in the 3D bone model, and outputting the 3D bone model in the coordinate system tracking the bone with the updated area of evolutive accuracy, for subsequent navigation of the bone in computer-assisted surgery.

14. The system according to claim 13, further comprising generating the 3D bone model from X-ray images specific to the patient includes generating the 3D bone model from only two X-ray images.

15. The system according to claim 13, wherein registering the landmark points in the area of evolutive accuracy includes registering the landmark points at a distance of 5±3 mm.

16. The system according to claim 15, wherein registering the landmark points in the area of expected high accuracy includes registering the landmark points at a distance of 20±4 mm.

17. The system according to claim 13, wherein registering one of the landmark points in the area of evolutive accuracy occurs between registering two of the landmark points in the area of expected high accuracy.

18. The system according to claim 13, wherein assessing the accuracy of the landmark points in the area of the evolutive accuracy includes verifying if the additional landmark points fall within tolerances of the area of the evolutive accuracy.

19. The system according to claim 18, wherein verifying if the landmark points fall within tolerances of the area of the evolutive accuracy includes rejecting at least one of the landmark points and registering at least another one of the landmark points in proximity to a rejected landmark point.

20. The system according to claim 19, wherein outputting the 3D bone model includes displaying the 3D bone model with the updated area of evolutive accuracy.

21. The system according to claim 1, wherein the area of expected high accuracy in the 3D bone model are parts of a bone visible directly from a point of view of imaging equipment, and the area of evolutive accuracy in the 3D bone model are parts of the bone not visible directly from a point of view of imaging equipment.

* * * * *